United States Patent [19]

Grieder

[11] 4,034,043
[45] July 5, 1977

[54] ALCOHOLIC HYDROLYSIS OF 2-FORMYLAMINOCHLOROTOLUENE

[75] Inventor: Alfred Grieder, Muttenz, Switzerland

[73] Assignee: Ciba-Geigy Corporation, Ardsley, N.Y.

[22] Filed: Jan. 13, 1976

[21] Appl. No.: 648,847

[52] U.S. Cl. ............................................. 260/578
[51] Int. Cl.² ..................................... C07C 87/50
[58] Field of Search .................................. 260/578

[56] References Cited

UNITED STATES PATENTS 1,930,754  10/1933  Havas et al. .................. 260/578 X
3,453,335  7/1969  Starnes ......................... 260/578 X

OTHER PUBLICATIONS

Sidgwick, "The Organic Chemistry of Nitrogen", p. 234 (1966).

Primary Examiner—Daniel E. Wyman
Assistant Examiner—John J. Doll
Attorney, Agent, or Firm—Karl F. Jorda

[57] ABSTRACT

An improved process for the production of 2-aminochlorotoluene hydrochloride comprising chlorination of 2-formyl-amino-toluene, splitting off the formyl group of the 2-formyl-amino-chlorotoluenes and isolation of crystalline 2-amino-5-chlorotoluene hydrochloride is disclosed, in which process the 2-formylamino-5-chlorotoluene formed by chlorination of 2-formylamino-toluene in an inert solvent is reacted with methanol to form 2-amino-5-chlorotoluene and methyl formate, and the 2-amino-5-chlorotoluene is isolated as hydrochloride.

6 Claims, No Drawings

ALCOHOLIC HYDROLYSIS OF 2-FORMYLAMINOCHLOROTOLUENE

The present invention relates to a process for the production of 2-amino-5-chlorotoluene hydrochloride.

2-Amino-5-chlorotoluene is a valuable intermediate for producing pesticidal active ingredients. It can for example be converted by reaction with thiophosgene into the corresponding isothiocyanate, which yields, on further reaction with dimethylamine, N-(2-methyl-4-chlorophenyl)-N',N'-dimethylthiourea, which is characterised by an excellent insecticidal and acaricidal action. Pest-control compositions containing this substance, and their use for combatting harmful insects and acarids, are described in the U.S. Pat. Nos. 3,801,635 and 3,395,233.

2-Amino-5-chlorotoluene can also be converted into the corresponding isocyanate which, on further reaction with dimethylformamide, yields N-(2-methyl-4-chlorophenyl)-N',N'-dimethylformamidine, which is eminently suitable for the control of ectoparasites, especially of mites and ticks, as well as for the control of cotton pests. Corresponding applications of N-(2-methyl-4-chlorophenyl)-N',N'-dimethylformamidine are described in the U.S. Pat. Nos. 3,462,537 and 3,629,460.

It is known that 2-amino-5-chlorotoluene can be produced by a process described in the U.S. Pat. No. 1,930,754, wherein chlorine is introduced into a solution of 2-formylaminotoluene in toluene, and the reaction product is subsequently hydrolyzed after the addition of water and aqueous hydrochloric acid. In the process, 2-amino-5-chlorotoluene is precipitable in the form of the hydrochloride, whilst undesirable by-products, such as 2-amino-3-chlorotoluene and 2-amino-3,5-dichlorotoluene, remain in solution. This known process is therfore unsatisfactory because there are formed during hydrolysis performed with aqueous hydrochloric acid under relatively severe conditions resinous by-products, which reduce the yield of desired final product and impair the quality thereof.

It is further known that 2-amino-5-chlorotoluene in the form of the hydrochloride is produced by a process wherein the substance mixture obtained by chlorination of 2-acetylamino-toluene, which mixture consists to the extent of 70% of 2-acetylamino-5-chlorotoluene and by-products, is refluxed for 3 hours in a mixture of ethanol and aqueous concentrated hydrochloric acid (Rev. Chim. 14 (11-12), 647-649, (1963); C.A. 605 a-d (1964)). In this process too there occur, as a consequence of the severe conditions that have to be applied, resinous by-products which decrease the yield of 2-amino-5-chlorotoluene and impair the purity of the final product.

A disadvantage of the two prior known processes mentioned is further that after hydrolysis there appear in the waste water the ecologically problematic cleavage products, formic acid and acetic acid.

The object of the present invention is therefore to provide a process which renders possible in a simple manner, under mild conditions and with the avoidance of the formation of by-products, the separation of pure 2-amino-5-chlorotoluene from the mixture of substances obtained on chlorination of 2-formylaminotoluene.

It has been found that from the reaction mixture obtained on chlorination of 2-formylaminotoluene in an inert solvent, the formed 2-amino-5-chlorotoluene hydrochloride can, in a simple manner and under mild conditions, be produced practically quantitatively and in a very pure form by a process wherein the 2-formylamino-5-chlorotoluene, formed on chlorination of 2-formylaminotoluene, in the reaction mixture obtained on chlorination is split by reaction with methanol into methyl formate and 2-amino-5-chlorotoluene, and the last-mentioned is separated as hydrochloride.

Suitable inert solvents for performing the process of the invention are chlorinated hydrocarbons such as methylene chloride, chloroform, carbon tetrachloride, ethylene dichloride and tetrachloroethane, chlorobenzene, O-dichlorobenzene; ethers such as diethyl ether, tetrahydrofuran and dioxane; and nitriles such as acetonitrile. A particularly suitable solvent for carrying out the process of the invention is chloroform.

Splitting of the 2-formylamino-5-chlorotoluene, formed on chlorination of 2-formylaminotoluene, with methanol is performed at a temperature of between 20° and 60° C, preferably at between 25° and 30° C. The reaction duration is about 1 to 2 hours.

On chlorination of 2-formylaminotoluene, 2-formylamino-5-chlorotoluene is formed in an amount of approximately 75% to 80% of theory. In addition, there are formed 2-formylamino-3-chlorotoluene and 2-formylamino-3,5-dichlorotoluene. After chlorination, the reaction mixture also contains a small amount of unreacted 2-formylaminotoluene. Since the formyl group of 2-formylamino-5-chlorotoluene is preferentially split off by methanol, the addition of the equivalent amount of methanol, relative to the 2-formylamino-5-chlorotoluene present in the chlorination mixture, is sufficient to completely split the 2-formylamino-5-chlorotoluene. Preferably, however, the splitting of the 2-formylamino-5-chlorotoluene present in the reaction mixture is performed with an excess of methanol. There is thus advantageously added 1.05 to 1.3 moles of methanol, preferably 1.2 moles of methanol, per mole of 2-formylamino-5-chlorotoluene present in the reaction mixture.

A preferred embodiment of the process of the invention comprises adding to a reaction mixture, obtained by chlorination of 2-formylaminotoluene in one of the aforementioned solvents, 0.85 to 0.90 mole of methanol per mole of employed 2-formylaminotoluene, and stirring the resulting mixture for 2 to 3 hours at 25° to 30° C. The precipitated 2-amino-5-chlorotoluene hydrochloride is afterwards filtered off. An addition of hydrogen chloride for the formation of the hydrochloride is not necessary since the reaction mixture already contains a sufficient amount of hydrogen chloride as by-product of the chlorination reaction.

The yields of 2-amino-5-chlorotoluene hydrochloride attainable with the process of the invention are between 69 and 73% of theory, relative to the amount of 2-formylaminotoluene used. It is possible with the process of the invention to practically completely convert, with the avoidance of secondary reactions, the 2-formylamino-5-chlorotoluene, formed on chlorination of 2-formylaminotoluene, into 2-amino-5-chlorotoluene hydrochloride; and to isolate this in a pure, crystalline form. In consequence of the avoidance of secondary reactions, the process of the invention produces yields of 2-amino-5-chlorotoluene hydrochloride that are higher than those produced by the processes hitherto known. A further advantage of the process of the invention is that it is preformed completely free from water, as a result of which the corrosion problems occurring in the carrying out of the known processes in an aqueous medium are avoided. Finally, a further advantage of the process of the invention in that there is formed, instead of the formic acid occurring as by-product in the processes performed in an aqueous medium, methyl formate, which is easily separated due to its low boiling point of 32° C. In contrast to the known processes, the process of the invention produces no contaminated waste water.

Considering the severe reaction conditions applied for the hydrolysis of the N-acylated chlorotoluidines in the known processes, it is surprising that the splitting reaction according to the invention with methanol proceeds, even under considerably milder conditions, rapidly and quantitatively. It is also surprising that under the reaction conditions according to the invention 2-formylamino-5-chlorotoluene is selectively split, whilst the 2-formylaminochlorotoluenes formed on chlorination practically do not react.

The process of the invention is further illustrated by the following Examples:

EXAMPLE 1

79 g (1.1 moles) of chlorine is introduced into a solution of 135 g (1 mole) of 2-formylaminotoluene in 500 ml of chloroform at 20° to 25° C in the course of 2 to 3 hours. After the addition of 28 g (0.88 mole) of methanol, the mixture obtained is stirred for 2 hours at 25° to 30° C, and the formed 2-amino-5-chlorotoluene hydrochloride is subsequently filtered off. There is obtained 130 g (73% of theory relative to 2-formylaminotoluene) of 2-amino-5-chlorotoluene hydrochloride. The content of 2-amino-5-chlorotoluene hydrochloride in the product is 98 to 99%.

EXAMPLE 2

The process described in Example 1 is repeated using various solvents. The attained yields, as well as the purity of the products obtained, are summarised in the following Table:

| Solvent | Yield % of theory | Content of 2-amino-5-chlorotoluene hydrochloride |
|---|---|---|
| acetonitrile | 72 | 98–99% |
| tetrahydrofuran | 73 | 98–99% |
| tetrachloroethylene | 69 | 91–99% |

I claim:
1. Process for the production of 2-amino-5-chlorotoluene hydrochloride by chlorination of 2-formylaminotoluene, subsequent splitting-off of the formyl group of the formed 2-formylaminochlorotoluenes, and separation of 2-amino-5-chlorotoluene as hydrochloride, in which process the 2-formylamino-5-chlorotoluene, formed on chlorination of 2-formylaminotoluene in an inert organic solvent, in the reaction mixture obtained on chlorination is split by reaction with methanol into methyl formate and 2-amino-5-chlorotoluene; and the last-mentioned is separated as hydrochloride.

2. Process according to claim 1, wherein the splitting of 2-formylamino-5-chlorotoluene with methanol is performed at a temperature of between 20° and 60° C.

3. Process according to claim 1, wherein the reaction of 2-formylamino-5-chlorotoluene with methanol is performed at 25° to 30° C.

4. Process according to claim 1, wherein there is added to a reaction mixture, obtained by chlorination of 2-formylaminotoluene in an inert organic solvent, 0.85 to 0.90 mole of methanol per mole of employed 2-formylaminotoluene; the mixture obtained is stirred for 2 to 3 hours at 25° to 30° C; and the precipitated 2-amino-5-chlorotoluene hydrochloride is separated.

5. Process according to claim 1, wherein the inert organic solvent used is methylene chloride, chloroform, carbon tetrachloride, ethylene dichloride, tetrachloroethane, chlorobenzene, O-dichlorobenzene, diethyl ether, tetrahydrofuran, dioxane or acetronitrile.

6. Process according to claim 1, wherein the solvent used is chloroform.

* * * * *